United States Patent
Papaionnou

[11] Patent Number: 5,855,205
[45] Date of Patent: Jan. 5, 1999

[54] DEVICE FOR AND METHOD OF CARRYING OUT OPTICAL MEASUREMENTS IN TURBID MEDIA

[75] Inventor: Dimitrios Papaionnou, Eindhoven, Netherlands

[73] Assignee: U.S. Philips Corporation, New York, N.Y.

[21] Appl. No.: 498,305

[22] Filed: Jul. 3, 1995

[30] Foreign Application Priority Data

Jun. 30, 1994 [EP] European Pat. Off. ............... 94201886

[51] Int. Cl.[6] ........................................................ A61B 5/00
[52] U.S. Cl. ........................... 128/664; 128/665; 356/349
[58] Field of Search .................... 128/664, 665, 128/633, 634; 356/433, 349; 250/330, 341.1, 341.7

[56] References Cited

U.S. PATENT DOCUMENTS

| 5,287,672 | 2/1994 | Chance et al. | 364/550 |
| 5,309,907 | 5/1994 | Fang et al. | 128/633 |
| 5,353,799 | 10/1994 | Chance | 128/664 |
| 5,416,582 | 5/1995 | Knutson et al. | 356/349 |

OTHER PUBLICATIONS

"Refraction of Diffuse Photon Density Waves", by M.A. O'Leary et al, Physical Review Letters, vol. 69, No. 18, 2 Nov. 1992, pp. 2658–2661.

"Highly Sensitive Object Location in Tissue Models with Linear In–Phase and Anti–Phase Multi–Element Optical Arrays in One and Two Dimensions", by B. Chance et al, Proc. Natl. Acad. Sci. USA, vol. 90, pp. 3423–3427, Apr. 1993.

"Propagation of Photon–Density Waves in Strongly Scattering Media Containing an Absorbing Semi–Infinite Plane Bounded by a Straight Edge" by J.B. Fishkin et al, vol. 10, No. 1/Jan. 1983, J. Opt. Soc. Am.A, pp. 127–140.

Primary Examiner—Marvin M. Lateef
Assistant Examiner—Eleni Mantis Mercader
Attorney, Agent, or Firm—Jack D. Slobod

[57] ABSTRACT

Device for carrying out optical measurements in turbid media (105), e.g. biological tissue (119), comprising a coherent light source (150), a modulator (101) to modulate the frequency of the light source (150) and a detector (108), being sensitive to a small band of the modulated light frequencies of the light source. Light source (104) and detector (107) are placed opposite each other in a turbid medium (105). Because the behavior of the transmission of the FM-modulated light in the medium can be described by means of a travelling wave the detector shows different amplitudes and phases of the FM-modulation as a function of the distance to the light source. From the measured amplitudes and phases characteristics of the turbid medium can be derived. By applying two groups of light sources and the modulation of one group of light sources is in phase opposition with the other group of light sources it is possible to detect objects in the turbid medium. The device offers possibilities as a diagnostic tool for biological tissue, e.g. detection of tumors in mammal tissue.

19 Claims, 5 Drawing Sheets

DEVICE FOR AND METHOD OF CARRYING OUT OPTICAL MEASUREMENTS IN TURBID MEDIA

BACKGROUND OF THE INVENTION

1. Field of Invention

The invention relates to a device for carrying out optical measurements in turbid media, including at least one coherent light source, a detector unit and a control unit.

The invention also relates to a method of measuring biological tissues by irradiating the tissue by light from at least one light source.

The invention also relates to a method of determining inhomogeneities in biological tissues by irradiating the tissue by light from a plurality of light sources.

2. Description of the Related Art

A device of the kind set forth is known from M. A. O'Leary et al., Physical Review Letters, Vol. 69, No 18, November 1992.

The known device is used to study the propagation of diffuse light in turbid media with the object of developing applications for the localization of objects in turbid media. A turbid medium is to be understood to mean a medium in which the transport of light energy density can be described essentially by the diffusion equation. It has been found that an amplitude-modulated laser source generates a travelling wave of the light energy density in a turbid medium. These waves are referred to as photon density waves. Photon density waves are scalar, damped travelling waves. Even though the waves are quickly attenuated, they have a defined wavelength, amplitude and phase at all points in the medium. A diffusion coefficient for light in the turbid medium and an absorption coefficient in the turbid medium can be determined from the amplitude and the phase. In a biomedical environment the described technique offers possibilities in respect of imaging of inhomogeneities in objects, for example small breast tumors.

It is a drawback of the known device that only one photon density wave is generated in the light source.

SUMMARY OF THE INVENTION

It is inter alia an object of the invention to generate several photon density waves of the same frequency and different phase via a single light source. This is also an alternative method of generating photon density waves. This enables improved localization of inhomogeneities for applications aiming to localize inhomogeneities by means of several light sources.

A device of the kind set forth in accordance with the invention is characterized in that it comprises a frequency modulator which is coupled to the control unit in order to modulate a light source in a frequency band in response to a signal from the control unit, the detector unit being sensitive to light of frequencies from a part of the frequency band. As a result of this step, a first detector unit which is sensitive to light in a first frequency range within the frequency band observes an intensity modulation of the light in said first frequency range. The frequency of the intensity modulation equals the frequency of the modulating signal of the light source. The intensity modulation in a point in the turbid medium can be described by means of a first photon density wave.

If the detector unit has been rendered sensitive to light in another part of the frequency band, an intensity modulation will also be observed in the light. This modulation can be described by means of a second photon density wave which has a phase which deviates from that of the first photon density wave. Frequency modulation of the light source generates as if it were a photon density wave in a limited frequency range. A detector unit having an adequate passband within the frequency band will then observe a modulation of light with frequencies in said passband.

In order to distinguish these waves from normal or AM photon density waves, they are referred to as FM photon density waves. As opposed to AM photon density waves, where the frequency of the light source is kept constant and the amplitude is modulated, in the case of FM photon density waves the amplitude of the light source is kept substantially constant and the frequency is modulated.

A special embodiment of a device in accordance with the invention is characterized in that the frequency modulator is operative to modulate the frequency of the light source sinusoidally. As a result of this step, the spectrum is concentrated around $f_o \pm k\,f_m$, where $f_o$ is the light frequency of the laser used, $f_m$ is the modulation frequency and k is valued 1, 2, 3 ...

Another embodiment of a device in accordance with the invention is characterized in that the detector unit comprises an optical filter which transmits light of frequencies from a part of the frequency band. This step ensures that when an optical filter has a passband, for example in a range around $f_o + f_m$, an amplitude difference occurs in a detector signal due to incident frequency-modulated light.

A further embodiment of a device in accordance with the invention is characterized in that it comprises a number of light sources which are sub-divided into a first sub-group and a second sub-group, the frequency modulation of the second sub-group being in phase opposition relative to the frequency modulation of the first sub-group, the control unit enabling adjustment of the intensity of the first sub-group to a first value and the intensity of the second sub-group to a second value. As a result of this step, an interference pattern is generated by two photon density waves in phase opposition. In the near field, that is to say an area having a radius which is smaller than one wavelength of the photon density wave, an amplitude minimum and a maximum phase gradient can be measured in the interference pattern. The amplitude minimum and the maximum phase gradient can be shifted in the turbid medium by adjustment of different values of the first and the second intensity of the sub-groups. When the detector unit is provided with, for example two optical filters with a bandpass for a first and a second frequency range of the frequency band and when a light detector is arranged behind each optical filter, two interference patterns can be observed. Determination of the positions of the maximum phase gradients and the amplitude minima enables localization, on the basis of these positions, for example by averaging, of inhomogeneities which is more accurate than that offered by the determination of the amplitude minimum and the maximum phase gradient of an interference pattern generated by AM photon density waves. The latter method of establishing the presence of inhomogeneities from anomalies of an interference pattern of photon density waves is known from B. Chance, Proceedings National Academy of Science, U.S.A., Vol. 90, pages 3423–3427, April 1983, Medical Sciences.

A next embodiment of a device in accordance with the invention is characterized in that the successive light sources are arranged, at equal distances, along a line or in a regular polygon. As a result of this step, the position of a plane containing an amplitude minimum and a maximum phase gradient in the interference pattern is defined relative to the light sources and the detector unit.

Another embodiment of a device in accordance with the invention is characterized in that the light source comprises at least one laser which is coupled to an optical fiber or not. As a result of this step, a plurality of light sources can be created by way of optical power splitters in the optical fiber. A phase difference can be induced in the modulation between the first and the second sub-groups of light sources by way of length differences in the optical fiber between the two sub-groups.

Another embodiment of a device in accordance with the invention is characterized in that the detector unit comprises a light-sensitive diode or a photomultiplier tube.

When a photomultiplier tube is used, a signal can still be detected from light modulations with a very low light intensity.

A method in accordance with the invention is characterized in that it comprises the following steps:
 a) activating the light source so as to generate frequency-modulated light in a frequency band;
 b) determining the amplitude and phase of the modulation of the light with frequencies in a part of the frequency band;
 c) determining parameters of the tissue from the amplitude and phase determined sub b).

This method determines the scattering coefficients and the absorption coefficients between the source and the detector unit, the source and the detector unit scanning the entire tissue or a part of the tissue. If desired, these coefficients can be visualized in a graph or an image.

Another method in accordance with the invention is characterized in that it comprises the following steps:
 a) activating a first sub-group of light sources so as to generate, with a first intensity, frequency-modulated light in a frequency band, and activating a second sub-group of light sources, so as to generate, with a second intensity, frequency-modulated light in the frequency band, the frequency modulation of the second sub-group of light sources being in phase opposition relative to the frequency modulation of the first sub-group of light sources;
 b) determining, in a position, an amplitude and a phase of a first modulation of the light with light frequencies in a first part of the frequency band and determining an amplitude and a phase of the second modulation of the light with light frequencies in a second part of the frequency band;
 c) determining at least a position of:
  a minimum of the amplitudes of the first modulation, or a minimum of the amplitudes of the second modulation, or
  a maximum phase gradient of the first modulation, or a maximum phase gradient of the second modulation;
 d) comparing the positions found with the positions obtained from a previously executed reference measurement.

This method enables fast detection of an anomaly in the tissue, after which more accurate methods, for example MRI or X-ray radiography, can be applied so as to localize the anomaly in the tissue. The above and other aspects of the invention will be described in detail hereinafter, by way of example, with reference to the drawing.

DETAILED DESCRIPTION OF THE PREFERRED EMBODIMENT

Figure 1A:
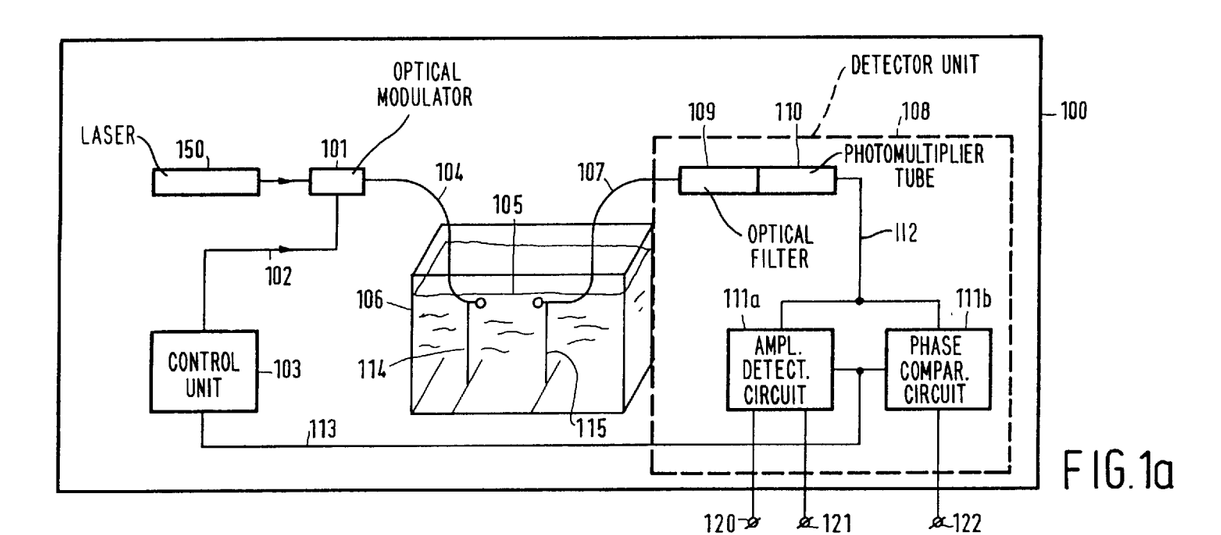
FIG. 1a shows a device in which the invention is used.

FIG. 1a shows a device 100 in accordance with the invention whereby FM photon density waves are generated. The light of a laser 150, having a wavelength of, for example about 760 nm, is conducted to the entrance of an optical modulator 101. The laser light is frequency-modulated by the optical modulator 101 with a sinusoidal signal 102 of, for example, 1000 MHz which originates from the control unit 103. The sinusoidal signal may also have a frequency other than said 1000 MHz, for example a frequency between 100 MHz and 2000 MHz, or have a shape other than said sinusoidal shape. A first optical fiber 104 conducts the light from the exit of the modulator 101 to a turbid medium 105. The turbid medium 105 is present in a holder 106. The end of the optical fiber 104 is mounted on a displaceable carrier 114 in the turbid medium 105 and faces the entrance of a second optical fiber 107 which is mounted on a second displaceable carrier 115 in the turbid medium 105, at some distance, for example 7 cm from the end of the first optical fiber 104. The light passing through the medium is intercepted by the second optical fiber 117 so as to be conducted to a detector unit 108. The detector unit 108 comprises an optical filter 109, a photomultiplier tube 110, an amplitude detection circuit 111a, and a phase comparison circuit 111b. The entrance of the optical filter 109 is situated at the end of the optical fiber 107 and the photomultiplier tube 110 is arranged at the exit of the optical filter. The filtered light is converted into a signal 112 by the photomultiplier tube 110. The amplitude detection circuit 111a and the phase comparison circuit 111b determine a d.c. component $A_{dc}$, an amplitude $A_{ac}$ and a phase $\Phi$ which are present, for example as voltages on the terminals 120, 121 and 122, respectively, from the signal 112 from the photomultiplier tube 110 and a reference signal 113 from the control unit 103. An alternative detector 111 comprises for example a heterodyne detector, an analog-to-digital converter and digital processing means. By heterodyning the detector signal with a reference signal of frequency $f_m+\delta f$, which is phase locked to the modulating signal 102, a low frequency signal is obtained. The d.c. component $A_{dc}$, an amplitude $A_{ac}$ and a phase $\Phi$ are obtained from this low frequency signal by means of an analog-to-digital converter and digital signal processing.

A model can be construed for the determination of the d.c. component $A_{dc}$, the amplitude $A_{ac}$ and the phase $\Phi$ in a point in the homogeneous turbid medium at a distance r from the source. This model is known from J. B. Fishkin, Journal Optical Society America, Vol. 10, No 1, January 1993. This model is based on the transport of the light energy density by means of a diffusion equation. For an infinite medium and a light source with a modulation angle frequency $\omega$, the wavelength of a photon density wave in a turbid medium is given by $$\lambda = 2\pi \left( \frac{v^2\mu_a^2 + \omega^2}{v^2 D^2} \right)^{-\frac{1}{4}} \left[ \sin\left( \frac{1}{2} \tan^{-1}\left( \frac{\omega}{v\mu_a} \right) \right) \right]^{-1}$$

in which v is the velocity of photons in the medium, $\mu_a$ is the linear absorption coefficient and D is the diffusion coefficient. D is given by $D=(3[\mu_a+\mu_s(1-g)])^{-1}$, in which $\mu_a$ is the linear absorption coefficient, $\mu_s$ is the linear scattering coefficient, and g is the mean value of the cosine of the scattering angle.

Using this model, the following formulas have been derived for $A_{dc}$, $A_{ac}$ and $\Phi$ for homogeneous media.

For $A_{dc}$:

$$\ln(A_{dc}) = -r\left(\frac{\mu_a}{D}\right)^{\frac{1}{2}} + \ln\left(\frac{S}{4\pi v D}\right) \quad (1)$$

For $A_{ac}$:

$$\ln(A_{ac}) = -r\left(\frac{v^2\mu_a^2 + \omega^2}{v^2 D^2}\right)^{\frac{1}{4}} \cos\left[\frac{1}{2}\tan^{-1}\left(\frac{\omega}{v\mu_a}\right)\right] + \ln\left(\frac{SA}{4\pi v D}\right) \quad (2)$$

For $\Phi$ $$\Phi = r\left(\frac{v^2\mu_a^2 + \omega^2}{v^2 D^2}\right)^{\frac{1}{4}} \sin\left[\frac{1}{2}\tan^{-1}\left(\frac{\omega}{v\mu_a}\right)\right] \quad (3)$$

in which v is the velocity of photons in the medium, D is the diffusion coefficient, $\mu_2$ is the linear absorption coefficient, $\omega$ is the angular frequency of the modulation, A is the amplitude of the modulation in the light source, and S is the number of photons per second. Subsequently, from measurements of $A_{dc}$, $A_{ac}$ and $\Phi$ the linear absorption coefficient $\mu_a$ and the linear scattering coefficient $\mu_s$ for homogeneous turbid media are derived by way of the formulas (1), (2) and (3).

Figure 1B:
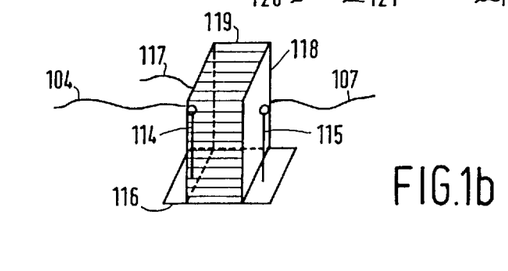
FIG. 1b shows an example of a holder for biological tissues.

FIG. 1b shows an alternative holder 116. The holder 106 and the turbid medium 105 in the devices 100 and 500 shown in FIGS. 1a and 5 herein can also be replaced by an alternative holder 116 and biological tissue 119, the shape of the alternative holder being adapted to the geometry of the biological tissue. The end of the optical fiber 104 is then arranged on the carrier 114 at a transparent exterior side 117 of the holder 116, and the entrance of the optical fiber 107 is arranged on a carrier 115 at the opposite transparent side 118 of the holder 116. During the measurements the light source, formed by the end of the optical fiber 104, and the entrance of the optical fiber 107, being aligned with respect thereto, are displaced along a number of points on the surface of the exterior sides 117 and 118, the d.c. component $A_{dc}$, an amplitude $A_{ac}$ and the phase $\Phi$ of the photon density wave then being determined. The absorption coefficients $\mu_s$ of a number of positions of the biological tissue are determined from these values.

Figure 2:
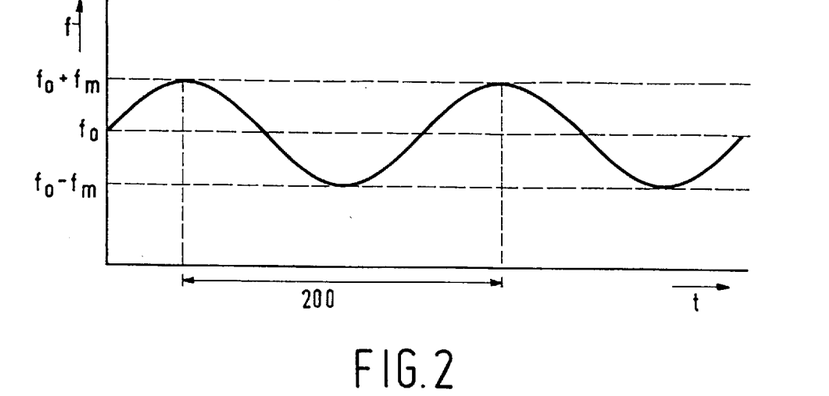
FIG. 2 shows a graph illustrating the frequency as a function of time of a frequency-modulated light source.

FIG. 2 shows a graph illustrating the light of a sinusoidally frequency-modulated light source. The time is plotted on the X-axis of this graph and the frequency of the emitted light is plotted on the Y-axis. The intensity of the laser light is substantially constant. It appears from the graph that the frequency varies sinusoidally in time between $f_o-f_m$ and $f_o+f_m$. It can also be deduced from the graph that for the frequency $f_o-f_m$ there is obtained a photon density wave whose period is denoted by the reference 200.

Figure 3:
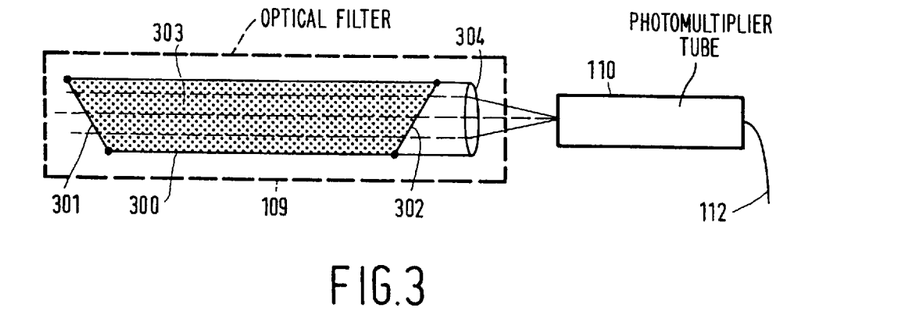
FIG. 3 shows a detector unit for a FM-photon density wave.
Figure 5:
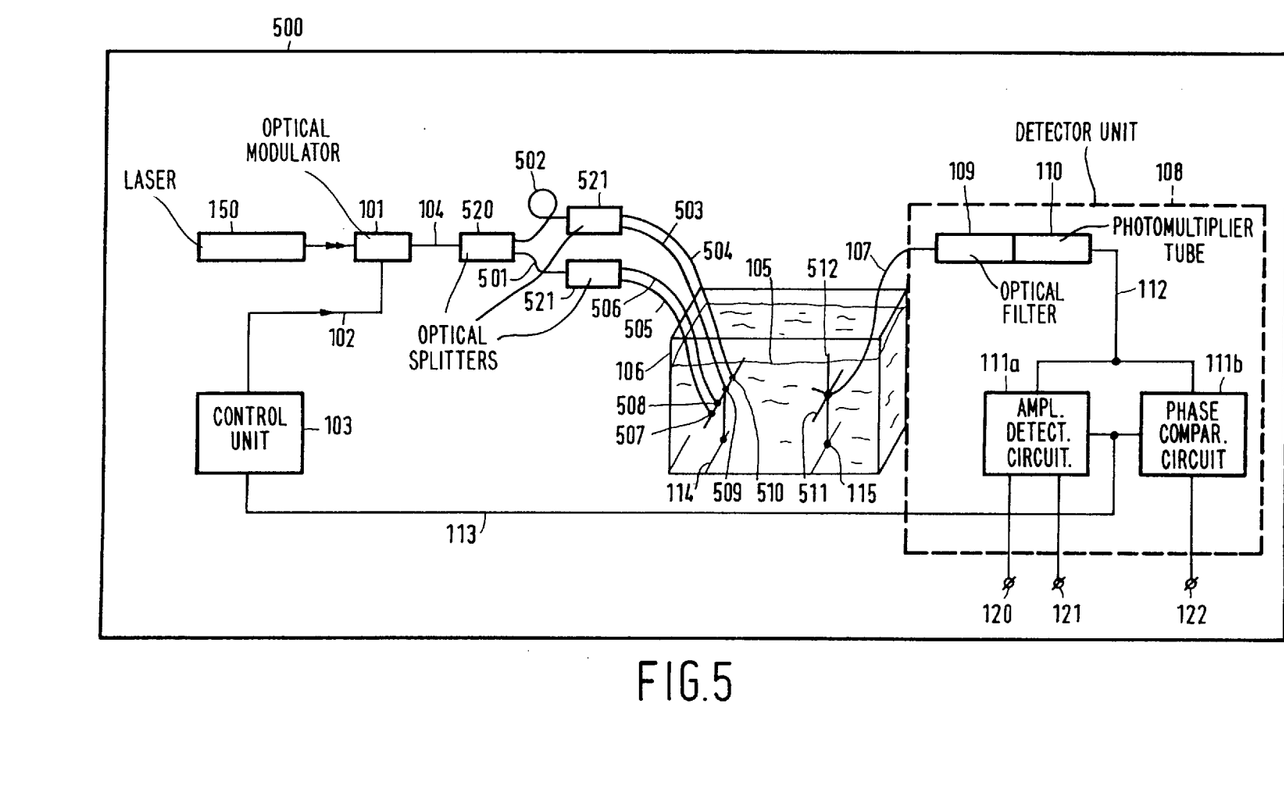
FIG. 5 shows a device comprising four light sources for carrying out a method in accordance with the invention.

FIG. 3 shows a detector unit for FM photon density waves comprising an optical filter 109 for use in combination with the photomultiplier tube 110. This optical filter is a molecular filter and comprises an elongate, scaled enclosure 300 with a transparent entrance window 301, a transparent exit window 302 which is arranged opposite the entrance window, and a lens 304. The enclosure 300 contains a molecular gas 303, for example oxygen $O_2$ at a pressure of 1 bar and at room temperature, for example 25° C. From the incoming light the molecular filter absorbs the spectral lines which correspond to the absorption spectrum of the gas used. If desired, the lines in the absorption spectrum of the gas can be slightly widened by using a higher gas pressure. The laser frequency can also be adapted slightly to the absorption spectrum of the gas by using a tunable laser 150 as shown in FIG. 5. The lens 304 concentrates the light emanating from the exit window 302 onto the photomultiplier tube 110.

Figure 4:
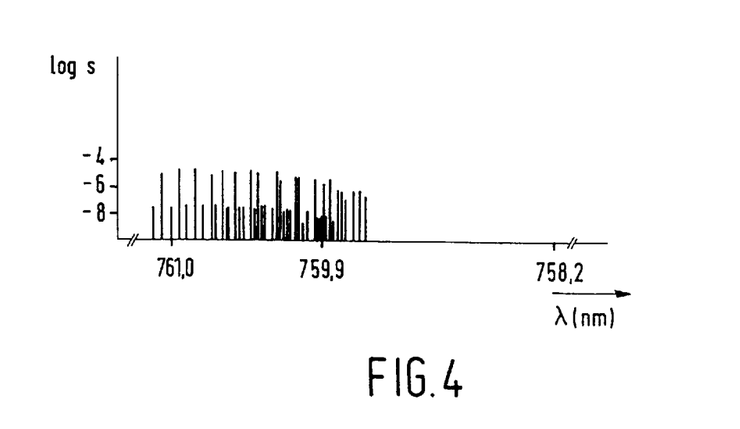
FIG. 4 shows a graph illustrating an absorption spectrum of an optical filter.

FIG. 4 shows a part of an absorption spectrum around 760 nm of a molecular filter comprising a gas-filled enclosure 300 which has a length of for example 35 cm and is filled with oxygen $O_2$ at a pressure of 1 bar and a temperature of 25° C. The graph shows that the absorption lines are very narrow. Therefore, the laser frequency $f_o$ will have to be very accurately adjusted to one of these absorption lines in order to obtain a difference in transmission between, for example the frequency $f_o-f_m$ and the frequency $f_o+f_m$.

FIG. 5 shows a second device 500 for carrying out a method in accordance with the invention. The laser light from the laser 150 is modulated in the same way as described with reference to FIG. 1a. The first optical fiber 104 conducts the light to an optical power splitter 520, for example a fiber optical coupler or a semi-transparent mirror in which the light is distributed between two optical fibers 501 and 502. The light is subsequently transported to a turbid media 105 via the second optical fiber 501, the third optical fiber 502, the optical power splitter 520, the two optical power splitters 521 and the optical fibers 503, 504, 505 and 506. Instead of each optical power splitter 21, being a 1 input to 2 output power splitter, it is also possible to use for each a 1 input to 4 output power splitter or a 1 input to 8 output power splitter to create respectively 8 or 16 light sources for a more homogeneous light distribution in the medium.

The optical path length of the second optical fiber 501 is shorter than the optical path length of the third optical fiber 502. The difference in optical path length equals to the distance the light traverses in the optical fiber in half a period of the modulation of the light in the optical fiber. The length of the optical fibers 503, 504, 505 and 506 is the same. The ends of the optical fibers 503, 504, 505, 506 constitute four light sources 507, 508, 509, 510 respectively. Due to the difference in optical path length of the optical fibers 501 and 502, the modulation of the light sources 507 and 508 is in phase opposition relative to the modulation of the light sources 509 and 510. The light sources 507, 508, 509 and 510 are arranged in a row, at a distance of, for example 2 cm from one another, on a displaceable carrier 114. At some distance, for example 7 cm, from and opposite the light sources 507, 508, 509 and 510 the entrance of the optical fiber 107 is mounted on a second displaceable carrier 115. The light traversing the medium 105 is conducted to a detector unit 108 via the optical fiber 107. The detector unit 108 determines the amplitude $A_{ac}$ and the phase $\Phi$ of the photon density wave. The photon density wave from the light sources 507 and 508 and that from the light sources 509 and 510 form an interference pattern in the turbid medium 105. An amplitude minimum and a maximum phase gradient can be determined in the near field in this interference pattern. In the case of equal intensity of the light sources 507 and 508 and the phase-opposition light sources 509 and 510, in a homogeneous turbid medium the positions of the amplitude minimum and the maximum phase gradient are situated in a plane through a perpendicular through the center of the positions of the light sources 507, 508, 509 and 510 and a line through the light sources. If necessary, the positions of the amplitude minimum and the maximum phase gradient can be shifted by variation of the intensity of the light sources 507 and 508 and the phase-opposition light sources 509 and 510. The presence of inhomogeneities is deduced from deviations between the theoretical and measured positions of the amplitude minimum and the maximum phase gradient. For example, it is also possible to determine an amplitude minimum and a maximum phase gradient of a reference medium and to compare these values with the values of the medium to be examined. These methods are known from an article by B. Chance at al., Proceedings Academy of Science, U.S.A., Vol. 90, pages 3423–3427, April 1993, Medical Sciences. More accurate determination of these positions is achieved, for example by utilizing different photon density waves of, for example, two light frequencies. The optical detector unit 600 is used, for this purpose.

Figure 6:
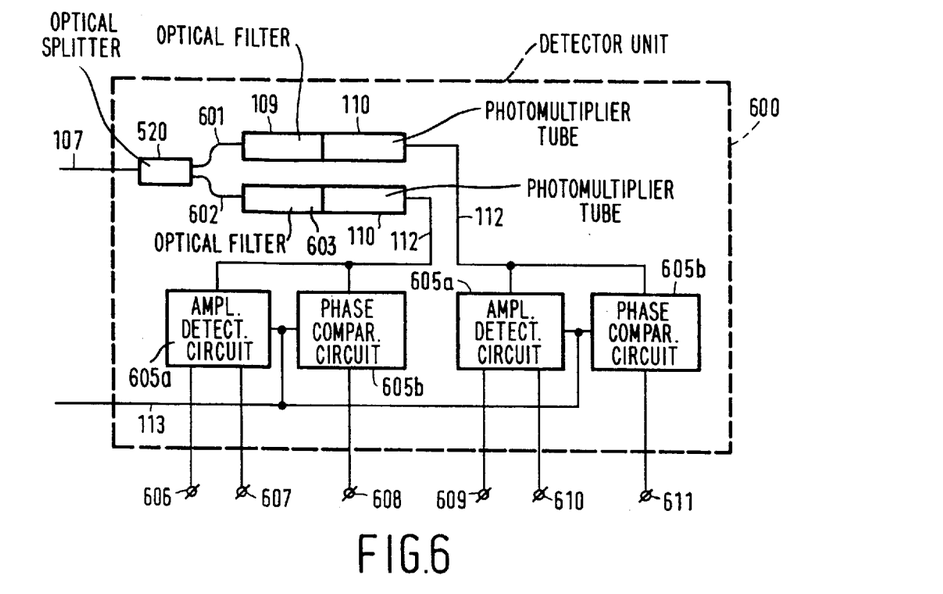
FIG. 6 shows a detector unit for photon density waves with two different light frequencies.

FIG. 6 shows an elaborate detector unit 600 for interference patterns of photon density waves for two light frequencies $f_o-f_m$ and $f_o+f_m$. The detector unit 600 comprises an optical splitter 520, for example a fiber-optical coupler or a semi-transparent mirror, two optical fibers 601 and 602, two optical filters 109 and 603, two photomultiplier tubes 110, and a processor unit 605. Optical fibers 601 and 602 transport the light to a first optical filter 109 and a second optical filter 603. The first optical filter 109 has a passband for a frequency $f_o-f_m$ and the second optical filter 103 has a passband for a frequency $f_o+f_m$. The exit of the first optical filter 109 is coupled to the first photomultiplier tube 110 and that of the second optical filter 603 is coupled to the second photomultiplier tube 110. Amplitude detection circuits 605a and phase comparison circuits 605b determine the amplitudes and phases $A_{dc1}$, $A_{ac1}$, $\Phi_1$ and $A_{dc2}$, $A_{ac2}$, $\Phi_2$ from the signals 112 from the photomultiplier tubes 110 and a reference signal 113. These values are available, for example, as voltages on the connections 606, 607, 608, 609, 610 and 611, respectively.

Figure 7:
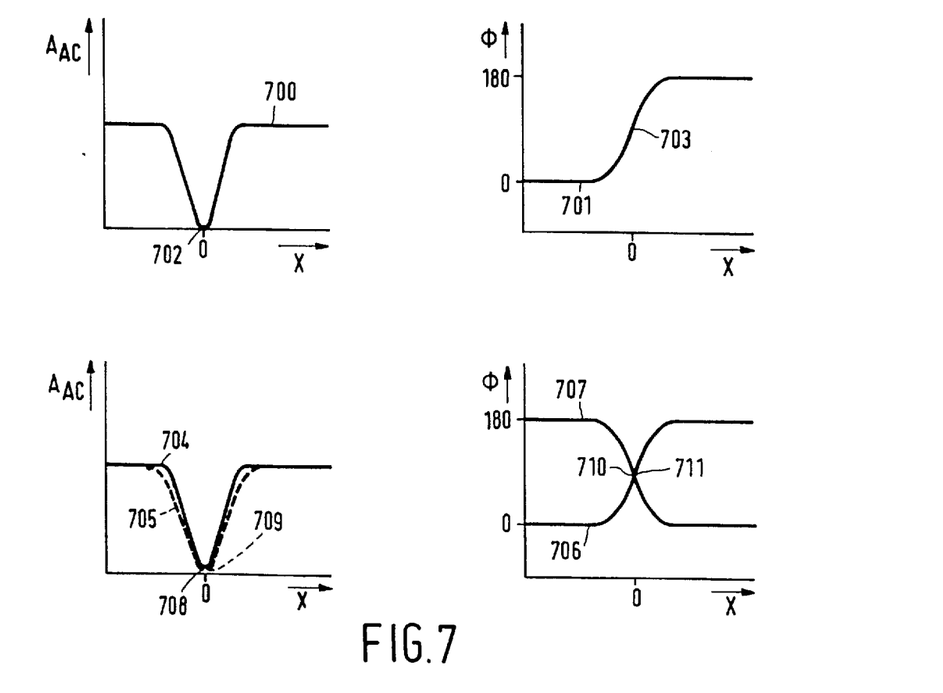
FIG. 7 shows graphs illustrating amplitudes and phases of interference patterns of photon density waves.

FIG. 7 shows the graphs 700, 701, 704, 705, 706 and 707 illustrating the amplitudes and phases of the various interference patterns. During measurements by means of a device 500 as described with reference to FIG. 5, the entrance of the optical fiber 107 is displaced through the turbid medium 105 along a line 511 which extends at some distance from and parallel to the light sources 507, 508, 509, 510, the amplitude $A_{ac}$ and the phase $\Phi$ of a photon density wave with a light frequency $f_o+f_m$ thus being determined. The amplitude $A_{ac}$ and the phase $\Phi$ are shown in the graphs 700 and 701. The amplitude exhibits a local minimum 702. The phase varies for example from 0° to +180° and has a maximum phase gradient 703.

Using a detector unit 600 as shown in FIG. 6, mounted in a device 500 as shown in FIG. 5, the graphs 704, 705, 706, and 707 of the amplitudes $A_{ac1}$, $A_{ac2}$ and the phases $\Phi_1$, $\Phi_2$ of two photon density waves with a light frequency $f_o-f_m$ and a light frequency $f_o+f_m$ are determined along the line 511. The points 708 and 709 represent the amplitude minima $A_{ac1}$ and $A_{ac2}$ of the photon density waves having the light frequency $f_o-f_m$ and $f_o+f_m$, respectively, and the points 710 and 711 represent the maximum phase gradients $\Phi_1$ and $\Phi_2$. The estimated position of the maximum phase gradient of the interference patterns is found, for example by averaging the position coordinates of the points 708, 709, 710 and 711.

Figure 8A:
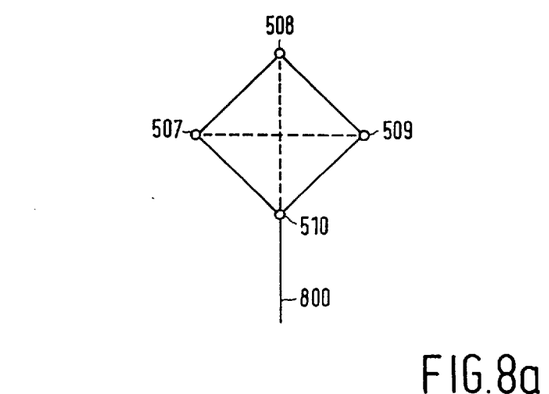
FIG. 8a shows a second example of a carrier with four light sources.

FIG. 8a shows a second set-up for frequency modulated light sources 507, 508, 509 and 510 for use in the device 500 described with reference to FIG. 5. In this second set-up the light sources 507, 508, 509 and 510 are mounted in a square, having a side of, for example 2 cm, on a carrier 800, the modulation of the light sources 507 and 508 being in phase-opposition relative to the modulation of the light sources 509 and 510. The photon density wave from the light sources 507 and 508 and that from the light sources 509 and 510 form an interference pattern in the turbid medium 105 in which an amplitude minimum and a maximum phase gradient can be determined for the near field. In the case of equal intensity of the light sources 507 and 508 and the phase-opposition light sources 509 and 510, in a homogeneous turbid medium the positions of the amplitude minima and the maximum phase gradient, are situated on a perpendicular through the center of the square formed by the light sources 507, 508, 509 and 510. The presence of inhomogeneities is derived from deviations between positions of the measured values and the theoretical values, for a homogeneous turbid medium, or reference values obtained from measurements of reference tissues. The interference patterns of photon density waves of two light frequencies $f_o-f_m$ and $f_o+f_m$ are observed by utilizing the detector unit 600. The detector unit 600 enables more accurate determination of the positions of the amplitude minimum and the maximum phase gradient.

Figure 8B:
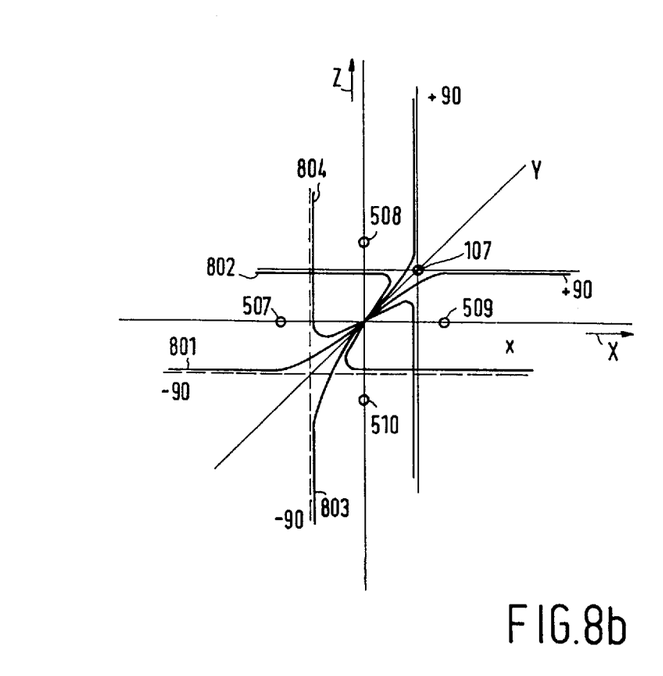
FIG. 8b shows a graph illustrating the phase of interference patterns generated by a device comprising four light sources arranged in a square.

FIG. 8b shows the graphs 801, 802, 803 and 804 determined by the detector unit 600 and illustrating the phases $\Phi_1$, $\Phi_2$, $\Phi_3$, $\Phi_4$ of an interference pattern generated by photon density waves originating from four frequency-modulated light sources 507, 508, 509 and 510 which are arranged in a square configuration in a device as shown in FIG. 5. The graphs 801 and 802 represent the phase $\Phi_1$ and $\Phi_2$ along a line 511 as shown in FIG. 5 at some distance from and parallel to a line through the light sources 507 and 509, respectively. The graphs 803 and 804 relate to the phases $\Phi_3$ and $\Phi_4$ along a line 512 (as shown in FIG. 5) at some distance from and parallel to a line through the light sources 508 and 510, respectively. The four positions of the maximum phase gradients of the interference patterns are used for more accurate determination of the position of the maximum phase gradient. The presence of inhomogeneities is established on the basis of deviations between the measured position of the amplitude minimum and the maximum phase gradient and the theoretical position of the amplitude and the maximum phase gradient. In the case of non-homogeneous media, reference values of the amplitude minimum and the phase gradient of healthy, non-homogeneous biological tissues are determined instead of the theoretical values. Deviations between the measured values and these reference values indicate anomalies in the tissue examined.

I claim:

1. A device for carrying out optical measurements in a turbid medium, comprising at least one coherent light source for irradiating the turbid medium with light, a detector unit for detecting light which is incident on the detector unit after exiting the turbid medium, a control unit, and a frequency modulator which is coupled to the control unit in order to frequency modulate the at least one light source over a frequency band of light frequencies in response to a modulation signal from the control unit so that the frequency of the light from the light source irradiating the turbid medium varies cyclically in frequency versus time, while the intensity of the light from the light source irradiating the turbid medium is maintained substantially constant, the detector unit being sensitive to light of frequencies from a part of the frequency band for detecting an intensity modulation appearing in the light unit within said part of the frequency band incident on the detector, which intensity modulation is of the same frequency as said cyclical variation.

2. A device as claimed in claim 1, wherein the detector unit comprises a phase comparison circuit for determining the phase of the intensity modulation of the light incident on the detector unit relative to the modulation signal, and also comprises an amplitude detection circuit for determining the amplitude of the intensity modulation of the light incident on the detector unit.

3. A device as claimed in claim 2, wherein the cyclical variation of frequency versus time is sinusoidal.

4. A device as claimed in claim 3, wherein the detector unit comprises an optical filter which transmits light of frequencies from a part of the frequency band.

5. A device as claimed in claim 4, further comprising a number of light sources which are subdivided into a first sub-group and a second sub-group and each of the light sources in the first and second sub-groups is frequency modulated, the frequency modulation of the light sources of the second sub-group being in phase opposition relative to the frequency modulation of the light sources of the first sub-group, the control unit adjusting the intensity of the light sources of the first sub-group to a first substantially constant value and the intensity of the light sources of the second sub-group to a second substantially constant value.

6. A device as claimed in claim 5, wherein the one or more light sources comprise a plurality of light sources which are arranged successively at equal distances.

7. A device as claimed in claim 2, wherein the detector unit comprises an optical filter which transmits light of frequencies from a part of the frequency band.

8. A device as claimed in claim 7, wherein the one or more light sources comprise a plurality of light sources which are arranged successively at equal distances.

9. A device as claimed in claim 7, further comprising a number of light sources which are subdivided into a first sub-group and a second sub-group and each of the light sources in the first and second sub-groups is frequency modulated, the frequency modulation of the light sources of the second sub-group being in phase opposition relative to the frequency modulation of the light sources of the first sub-group, the control unit adjusting the intensity of the light sources of the first sub-group to a first substantially constant value and the intensity of the light sources of the second sub-group to a second substantially constant value.

10. A device as claimed in claim 2, further comprising a number of light sources which are subdivided into a first sub-group and a second sub-group and each of the light sources in the first and second sub-groups is frequency modulated, the frequency modulation of the light sources of the second sub-group being in phase opposition relative to the frequency modulation of the light sources of the first sub-group, the control unit adjusting the intensity of the light sources of the first sub-group to a first substantially constant value and the intensity of the light sources of the second sub-group to a second substantially constant value.

11. A device as claimed in claim 1, wherein the cyclical variation of frequency versus time is sinusoidal.

12. A device as claimed in claim 11, wherein the detector unit comprises an optical filter which transmits light of frequencies from a part of the frequency band.

13. A device as claimed in claim 11, further comprising a number of light sources which are subdivided into a first sub-group and a second sub-group and each of the light sources in the first and second sub-groups is frequency modulated, the frequency modulation of the light sources of the second sub-group being in phase opposition relative to the frequency modulation of the light sources of the first sub-group, the control unit adjusting the intensity of the light sources of the first sub-group to a first substantially constant value and the intensity of the light sources of the second sub-group to a second substantially constant value.

14. A device as claimed in claim 1, further comprising a number of light sources which are subdivided into a first sub-group and a second sub-group and each of the light sources in the first and second sub-groups is frequency modulated, the frequency modulation of the light sources of the second sub-group being in phase opposition relative to the frequency modulation of the light sources of the first sub-group, the control unit adjusting the intensity of the light sources of the first sub-group to a first substantially constant value and the intensity of the light sources of the second sub-group to a second substantially constant value.

15. A device as claimed in claim 14, wherein the one or more light sources comprise a plurality of light sources which are arranged successively at equal distances.

16. A device as claimed in claim 1, wherein the light source comprises at least one laser which is coupled to an optical fiber.

17. A device as claimed in claim 1, characterized in that the detector unit comprises a light-sensitive diode or a photomultiplier tube.

18. A method of measuring biological tissue by irradiating the tissue with light from at least one light source comprising the following steps:
   a) controlling the at least one light source so as to generate frequency-modulated light irradiating the tissue with a substantially constant intensity but with a frequency which varies cyclically versus time in a frequency band of light frequencies;
   b) determining the amplitude and phase of intensity modulation appearing in light exiting the tissue with frequencies in a part of the frequency band, which intensity modulation in said part of the frequency band is at the same frequency as said cyclical variation; and
   c) determining parameters of the tissue from the amplitude and phase determined in step b.

19. A method of determining inhomogeneities in biological tissue by irradiating the tissue with light from a plurality of light sources comprising the following steps:
   a) controlling a first sub-group of light sources so as to generate from each, with a first substantially constant intensity, frequency-modulated light which varies in frequency versus time in accordance with a first cyclical variation in a frequency band of light frequencies, and a second sub-group of light sources so as to generate from each, with a second substantially constant intensity, frequency-modulated light which varies in frequency versus time in accordance with a second cyclical variation in the frequency band which is at the same frequency as, and in phase opposition with, said first cyclical variation;

b) determining, in a position, an amplitude and a phase of a first intensity modulation of the light with light frequencies in a first part of the frequency band and determining an amplitude and a phase of a second intensity modulation of the light with light frequencies in a second part of the frequency band, which first and second intensity modulations are at the same frequency as said first and second cyclical variations;

c) determining a position of an extremum of at least one of the first modulation and the second modulation; and d) comparing the positions found with the positions obtained from a previously executed reference measurement.

\* \* \* \* \*